United States Patent
Cho et al.

(10) Patent No.: US 9,493,652 B2
(45) Date of Patent: Nov. 15, 2016

(54) POLYMERIC FILM COMPOSITION FOR NON-ENZYMATIC GLUCOSE SENSOR AND NON-ENZYMATIC GLUCOSE SENSOR INCLUDING THE SAME

(71) Applicants: SAMSUNG ELECTRONICS CO., LTD., Suwon-si (KR); INSTITUTE FOR RESEARCH & INDUSTRY COOPERATION, PNU, Busan (KR)

(72) Inventors: Chulho Cho, Seongnam-si (KR); Yoon-Bo Shim, Busan (KR); Jaehong Kim, Incheon (KR); Suntae Jung, Yongin-si (KR); Seongje Cho, Suwon-si (KR); Jaegeol Cho, Yongin-si (KR)

(73) Assignees: SAMSUNG ELECTRONICS CO., LTD., Suwon-si (KR); INSTITUTE FOR RESEARCH & INDUSTRY COOPERATION, PNU, Busan (KR)

( * ) Notice: Subject to any disclaimer, the term of this patent is extended or adjusted under 35 U.S.C. 154(b) by 0 days.

(21) Appl. No.: 14/555,169

(22) Filed: Nov. 26, 2014

(65) Prior Publication Data

US 2015/0144486 A1    May 28, 2015

(30) Foreign Application Priority Data

Nov. 27, 2013  (KR) .......................... 10-2013-0145676

(51) Int. Cl.
| | |
|---|---|
| *G01N 27/40* | (2006.01) |
| *C08L 81/06* | (2006.01) |
| *G01N 27/327* | (2006.01) |
| *C08K 5/55* | (2006.01) |
| *C08L 75/04* | (2006.01) |
| *C09D 175/04* | (2006.01) |

(52) U.S. Cl.
CPC .................. *C08L 81/06* (2013.01); *C08K 5/55* (2013.01); *C08L 75/04* (2013.01); *C09D 175/04* (2013.01); *G01N 27/3277* (2013.01)

(58) Field of Classification Search
CPC ....... C08K 5/55; C08L 75/04; C08L 81/006; G01N 27/40
See application file for complete search history.

(56) References Cited

U.S. PATENT DOCUMENTS

2009/0301876 A1* 12/2009 Wagner et al. ............... 204/415
2012/0258467 A1* 10/2012 Chinnayelka et al. ........ 435/7.1

FOREIGN PATENT DOCUMENTS

JP       10-2012-0022270 A      3/2012
KR          10-0765438 B1      10/2007

OTHER PUBLICATIONS

Lee et al. IEEE Sensors Journal, 2008, 1922.*
Schuvailo et al. Analytica Chimica Acta, 2006, 110-116.*
Das et al. Electroanalysis, 2011, 2036-2041.*
Jin et al; "Controlling anisotropic nanoparticle growth through plasmon excitation"; Nature; Oct. 2, 2003; 2 pgs.
Golberg et al; "Copper-Filled Carbon Nanotubes: Rheostatlike Behavior and Femtogram copper Mass Transport"; Advanced Materials; Aug. 3, 2007; 1 pg.
Bochris et al; "Suface Electorchemistry: A Molecular Level Approache"; Plenum Press; 1993; 1 pg.
Gutes et al; "Silver Dendrites from Galvanic Displacement on Commercial Aluminum Foil as an Effective SERS Substrate"; Journal of the American Chemical; Jan. 14, 2010; 2 pgs.
Sahoo et al; "Electric field directed self-assembly of cuprous oxide nanostructures for photon sensing"; ACS Nano; Dec. 22, 2009; 1 pg.
Kawasaki et al; "Synthesis of Platinum Dendrites and Nanowires via Directed Electrochemical Nanowire Assembly"; Nano Letters; 2011; 5 pgs.
Lim et al; "Pd—Pt Bimetallic Nanodendrites with High Activity for Oxygen Reduction"; Science; May 14, 2009; 2 pgs.
Wang et al; "Facile Synthesis and Electrochemical Properties of Intermetallic PtPb Nanodenfrites"; Chem. Mater.; 2009; 3 pgs.
Noh et al; "Application of a Cu—Co alloy dendrite on glucose and hydrogen peroxide sensors"; Electrochimica Acta 61; 2012; 8 pgs.
Toghill et al; "Electrochemical Non-enzymatic Glucose Sensors: A Perspective and an Evaluation"; International Journal of Electrochemical Science; 2010; pp. 1246-1301; 56 pgs.

* cited by examiner

*Primary Examiner* — Gurpreet Kaur
(74) *Attorney, Agent, or Firm* — Sughrue Mion, PLLC (57) ABSTRACT

A polymeric film composition and a non-enzymatic glucose sensor including the functional polymeric film are provided. The polymeric film composition includes polyurethane and perfluorosulfonic acid polymer.

12 Claims, 7 Drawing Sheets

POLYMERIC FILM COMPOSITION FOR NON-ENZYMATIC GLUCOSE SENSOR AND NON-ENZYMATIC GLUCOSE SENSOR INCLUDING THE SAME

CROSS-REFERENCE TO RELATED APPLICATION

This application claims priority from Korean Patent Application No. 10-2013-0145676, filed Nov. 27, 2013, the entire disclosure of which is hereby incorporated by reference.

BACKGROUND

1. Field

The present disclosure relates to a polymeric film for a non-enzymatic glucose sensor and, more particularly, to a polymeric film and a glucose sensor comprising the polymeric film, in which the number of interactions between the saccharides other than glucose and the non-enzymatic glucose sensor are reduced by the polymeric film, making it possible to improve sensor selectivity to glucose and minimize the interactions between the organic materials and the non-enzymatic glucose filter that would otherwise present obstacles to measurement.

2. Description of the Related Art

Characteristics of diabetes, including hyperglycemia (a defect in insulin secretion and abnormal insulin action levels) and complications thereof (injuries to eyes, kidneys, nerves, the heart, or blood vessels) have come to the forefront nationally and socially, and diabetes has been recognized as being a serious disease. As a result, there is a great deal of effort set forth for preventing and delaying the onset of chronic complications from diabetes. For this reason, it is very important for a selection of a treatment method and prognosis to be able to estimate the suitability of the treatment via continuous observation of blood sugar, and then quickly apply the result thus obtained to a treatment process. Therefore, blood sugar should be closely managed in a patient with diabetes, and rapid examination should be carried out so as to enable quick diagnosis and estimation of a treatment by a medical team. To this end, self-monitored blood sugar measurement has been increased. To achieve this, a study of a self-monitoring sensor and a system of blood sugar measurement is actively in progress.

An electrochemical sensor is the simplest sensor in terms of its signal conversion process, because it converts specific information into an electric signal. An electrochemical sensor does not require a fixed space or an elaborate alignment, unlike those methods that use light; it is not as affected by external vibration as measurements of mass or mechanical changes; and it can be operated with high sensitivity within a very broad range of concentrations. Since the whole of the electrochemical measuring device, as well as a detection part thereof, can be easily miniaturized and integrated at low cost, an electrochemical measuring device is a most preferred industrial means of measurement so long as it exhibits sufficient performance. The downside of electrochemical measurement is insufficient selectivity, and as a result, an electrochemical measuring device should be in contact with a sample. In the case of measuring a human body, this means that measurement should be mostly performed via an invasive inspection.

As the concept of biosensors has developed, new testing methodology has been proposed, in which the selectivity problems of electrochemical sensors can be solved by combining biomaterials with an electrode. As an example, there is an enzyme electrode. Most bio-enzymes selectively bind and react only to a specific substrate. Therefore, selectivity problems may be solved by fixing an enzyme on an electrode, and then indirectly measuring the chemical environment that is changed by the enzyme reaction.

A commercialized enzymatic glucose sensor is based on such a principle, i.e., that of an enzyme electrode. However, the activity of biomaterials in general, and enzymes in particular, are too sensitive to the influences resulting from their structural environments. The activity of a manufactured example is therefore infinitely worse than what would have been initially expected. Even in the case of a glucose sensor according to the most successful manufactured examples, the cost for using an enzyme is overwhelmingly high as compared to a sensor that does not use biomaterials. The causes of increased cost may include quality management during mass production, limitations arising from expiration dates, packaging costs, and oxygen concentration dependence. Using an enzyme increases these costs. Therefore, even though a lot of improvements have been achieved, a fundamental breakthrough in this technology has not yet been revealed. As an alternative way to overcome the disadvantages enzymatic sensors, a study involving a non-enzymatic glucose sensor that uses carbon nanotubes, nanoparticles, Pt, nanoporous Au, a metal-oxide electrode, and the like is in process. However, the selectivity problem of such a non-enzymatic glucose sensor has not been solved, and thus, such a sensor is not being used. It is therefore necessary to develop a new non-enzymatic glucose sensor that solves the disadvantages of conventional enzymatic sensors by using a metal electrode.

An earlier study on non-enzymatic electrochemical oxidation of saccharides focused on the use of generally-used electrode materials, such as C, Cu, Ni, Fe, Pt, and Au (see R. Jin, Y. C. Cao, E. Hao, G. S. Metraux, G. C. Schatz, C. A. Mirkin, *Nature* 425 (2003) 487; D. Golberg, P. M. F. J. Costa, M. Mitome, S. Hampel, D. Haase, C. Mueller, A. Leonhardt, Y. Bando, *Adv. Mater.* 19 (2007) 1937). However, these materials cause fundamental problems of, for example, low efficiency and toxicity as a result of a chemically adsorbed intermediate. Therefore, it is necessary to develop an ideal material that is capable of promoting the oxidation of saccharides such as glucose while also overcoming the above-mentioned problems. Thus, metal catalysts are receiving focused attention. Studies on the structures of various types, such as nanoparticles (Au, Pt (see J. O'M. Bochris, S. U. M. Khan, *Surface Electrochemistry*, Plenum Press, New York, USA, 1993)), a single dendrite (Ag (see A. Gutes, C. Carraro, R. Maboudian, *J. Am. Chem. Soc.* 132 (2010) 1476), Cu (see S. Sahoo, S. Husale, B. Colwill, T. M. Lu, S. Nayak, P. M. Ajayan, *ACS Nano* 3 (2009) 3935), Pt (see J. K. Kawasaki, C. B. Arnold, *Nano Lett.* 11 (2011) 781)), and an alloy dendrite (Pd—Pt (see B. Lim, M. Jiang, P. H. C. Camargo, E. C. Cho, J. Tao, X. Lu, Y. Zhu, Y. Xia, *Science* 324 (2009) 1302), Pd—Ag (see J. Huang, S. Vongehr, S. Tang, H. Lu, X. Meng, *J. Phys. Chem. C* 114 (2010) 15005), Pt—Pb (see J. Wang, R. M. Asmussen, B. Adams, D. F. Thomas, A. Chen, *Chem. Mater.* 21 (2009) 1716), Cu—Co (see H.-B Noh, K.-S. Lee, P. Chandra, M.-S. Won, Y.-B. Shim, *Electrochimica Acta* 61 (2012) 36)) have been carried out. Among them, the structure of an alloy dendrite has high oxidation catalyst function due to a unique layer structure having very high surface area and several active sites, and thus, is possible for it to be used as a non-enzymatic glucose oxidation catalyst (see K. E. Toghill, R. G. Comton, *Int. J. Electrochem. Sci.* 5 (2010) 1246)].

In the case of an enzymatic glucose sensor, there is a technical limitation in that variations in properties are present as a result of deteriorations of the enzyme and differences between temperatures and production lots (batch). To overcome this, many studies of non-enzymatic glucose sensors are in progress, but because of the properties thereof, other saccharides and organic materials (ascorbic acid (AA) and acetaminophen (AP)) other than glucose may be oxidized, and thus, there exists a need to solve the selectivity problem of making a sensor that is selective only to glucose.

As one method for solving the issue of such selectivity, a study of a functional film capable of selectively passing glucose is required, and until now, for removing the blocking actions of organic materials (AA, AP), a study on the use of a functional protection film (for example, Nafion®, Kel-F, cellulose acetate, chitosan, poly(ethyleneimine), polyurethane, and the like) to a metal or metal oxide (nanoporous Pt) electrode has been reported. However, until now, a study on a polymeric film for increasing the selectivity of glucose from among various saccharides has not been reported.

SUMMARY

One or more exemplary embodiments provide a polymeric film for improving saccharides selectivity and the sensitivity of a non-enzymatic glucose sensor, and also to overcome the blocking action of organic materials, and a glucose sensor including the polymeric film.

In order to achieve the above-mentioned object, the present inventors conducted a thorough investigation with regard to a functional film for improving selectivity and sensitivity of a non-enzymatic glucose sensor to glucose, and as a result, the inventors found when a polymeric film having a specific composition according to the present disclosure is used, the problem of oxidizing saccharides other than glucose is significantly reduced, and the blocking actions of organic materials, such as ascorbic acid (AA) and acetaminophen (AP), are also removed. Thus, a glucose sensor having excellent selectivity to glucose and also excellent sensitivity can be provided.

According to an aspect of an exemplary embodiment, there is provided a polymeric film composition for a non-enzymatic glucose sensor comprising polyurethane and a perfluorosulfonic acid polymer.

The perfluorosulfonic acid polymer may be Nafion®, a product manufactured by DuPont.

The perfluorosulfonic acid polymer may be Aciplex®, manufactured by Asahi Chemical, Flemion®, manufactured by Asahi Glass Company, sulfonated styrene-ethylene-butylene-styrene (SEBS), sulfonated styrene-ethylene, poly arylene ether sulfone, sulfonated poly arylene ether ether ketone (PEEK), sulfophenylated polysulfone, or poly sodium 4-styrenesulfonate (PSS).

The above-described Nafion® may be represented by the following Chemical Formula 1.

Chemical Formula 1

Polyurethane, as disclosed herein, is obtained by reacting polyols and polyisocyanates. As a polyol, any kind of polyol may be used, and the type is not particularly limited, as long as it has two or more hydroxyl groups per molecule. Examples of the polyol may include one or more of polyester polyol, polyether polyol, polycarbonate diol, and the like. It may be used singly or in combinations of two or more.

The polyol may be at least one selected from the group consisting of ethylene glycol, 1,2-propane diol, 1,3-propane diol, 1,3-butane diol, 1,4-butane diol, neopentyl glycol, pentane diol, 1,6-hexane diol, 1,8-octane diol, 1,10-decane diol, 4,4'-dihydroxy phenyl propane, 4,4'-dihydroxy methyl methane, diethylene glycol, triethylene glycol, polyethylene glycol, dipropylene glycol, polypropylene glycol, 1,4-cyclohexane dimethanol, 1,4-cyclohexane diol, bisphenol A, bisphenol F, glycerin, 1,1,1-trimethylol propane, 1,2,5-hexanetriol, pentaerythritol, glucose, sucrose, and sorbitol.

A polyester polyol may be obtained by reacting polybasic acid components and polyol components. Examples of the polybasic acid components may include aromatic dicarboxylic acids such as ortho-phthalic acid, isophthalic acid, terephthalic acid, 1,4-naphthalene dicarboxylic acid, 2,5-naphthalene dicarboxylic acid, 2,6-naphthalene dicarboxylic acid, biphenyl dicarboxylic acid, and tetrahydrophthalic acid; aliphatic dicarboxylic acids such as oxalic acid, succinic acid, malonic acid, glutaric acid, adipic acid, pimelic acid, suberic acid, azelaic acid, sebacic acid, linoleic acid, maleic acid, fumaric acid, mesaconic acid, and itconic acid; alicyclic acids such as hexahydrophthalic acid, tetrahydrophthalic acid, 1,3-cyclohexanedicarboxylic acid, and 1,4-cyclohexanedicarboxylic acid; or reactive derivatives such as acid anhydride, alkyl ester, and acid halides thereof. They may be used singly or in combinations of two or more. In addition, they may be at least one selected from the group consisting of polytetramethylene glycol (PTMG), polypropylene glycol (PPG), and polyethylene glycol (PEG).

The polycarbonate polyol may be at least one selected from the group consisting of poly(hexamethylene carbonate) glycol and poly(cyclohexane carbonate)glycol.

The polyether polyol may be obtained by adding alkylene oxide to polyhydric alcohol via a ring-opening polymerization. Examples of the polyhydric alcohol may include ethylene glycol, diethylene glycol, propylene glycol, dipropylene glycol, glycerin, trimethylolpropane, and the like. They may be used singly or in combinations of two or more.

The isocyanate is not limited as long as it has two or more NCO groups, and example thereof may be one or, in combination, two or more selected from the group consisting of toluene diisocyanate (TDI), 4,4-diphenylmethane diisocyanate (MDI), 1,5-naphthalene diisocyanate (NDI), tolidine diisocyanate (TODI), hexamethylene diisocyanate (HMDI), isophorone diisocyanate (IPDI), p-phenylene diisocyanate, trans cyclohexane, 1,4-diisocyanate, and xylene diisocyanate (XDI).

The polymeric film composition may include 1.0 wt % to 5.0 wt %, for example, 3.0 wt % of the sum weight of the polyurethane and the perfluorosulfonic acid polymer with respect to the total weight of the composition. When the above-described content is not within the above-described range, selectivity to saccharides other than glucose is increased, and thus, there is a problem in that the sensor's selectivity to the target glucose is decreased. As for the weight ratio of the perfluorosulfonic acid polymer and polyurethane, the ratio of perfluorosulfonic acid polymer:

polyurethane may be 1:1. When the ratio is not the above described ratio, the selectivity to glucose is decreased, which may be a problem.

The polymeric film composition may further include amino phenyl boronic acid (APBA). The amino phenyl boronic acid makes it possible to improve the sensitivity of the glucose sensor.

The amino phenyl boronic acid may be included in an amount of 0.05 wt % to 0.3 wt %, for example, 0.1 wt % with respect to the total weight of the composition. When the amount of amino phenyl boronic acid is 0.05 wt % or more, it is possible to improve the sensitivity of the glucose sensor, and when it is 0.3 wt % or less, the oxidation reaction by a non-enzymatic catalyst of a non-enzymatic glucose sensor is not inhibited.

According to an aspect of another exemplary embodiment, there is provided a non-enzymatic glucose sensor characterized in that a reference electrode, a working electrode electrically connected to the reference electrode, and a polymeric film provided on the surface of the working electrode are included, and the polymeric film is formed by the above-described polymeric film composition.

The non-enzymatic sensor may have the structure of a general non-enzymatic glucose sensor.

The reference electrode may be an Ag/AgCl electrode, but the present disclosure is not limited thereto.

The non-enzymatic glucose sensor may further comprise an indicator electrode. The indicator electrode may be a platinum electrode, but the present invention is not limited thereto.

The polymeric film may be formed by drying the polymeric film composition at 25° C. to 75° C., for example, 50° C. Within the above-described temperature range, selectivity to glucose is most excellently exhibited.

The polymeric film composition is dried after dropping it on the working electrode.

The surface of the working electrode is made from a single metal or an alloy formed from a plurality of metals.

The metals on the surface of the working electrode may be made from a single metal or an alloy of two or more of the single metals selected from the group constituting of Cu, Au, Zn, Mn, Ni, and Co. As long as the metal may be used as an oxidation catalyst of glucose, it is not particularly limited.

The surface of the working electrode is made from a Cu—Co alloy.

As for the atomic metal content ratio of Cu and Co on the surface of the working electrode, Cu may be present in an amount of from 45 to 65% and Co may be present in an amount of 35% to 55%, and for example, Cu may be present in an amount of 45 to 60% and Co may be present in an amount of 40% to 55%.

The working electrode is a microporous metal electrode.

In the present disclosure, the term "microporous metal electrode" means a metal electrode having a porous surface comprising fine pores.

The diameter of the pores may be from 100 nm to 5 μm.
The porosity of the pores may be from 5% to 15%.
The working electrode may be a dendrite electrode.

In the present disclosure, the term "dendrite electrode" means an electrode in which a metal or an alloy of two or more of metals is grown using a method of applying current on the electrode surface.

The shape of the grown alloy may be in the shape of a leaf.

The working electrode may be formed on a glassy carbon electrode or copper plate via electrical deposition.

In more detail, the working electrode may be made with a Cu—Co alloy dendrite electrode.

In the case where the working electrode is a Cu—Co alloy dendrite electrode, the electrode may be formed on a glassy carbon electrode or copper plate via electrical deposition at a potential of −0.6 V to −1.2 V for 75 to 200 seconds, for example, a potential of −0.8 V for 100 seconds. If the applied potential exceeds −0.6 V, the amount of alloy may be low and the alloy may be in the form of particles, whereas if the applied potential is less than −1.2 V, there may be a problem in that many agglomerations of particles may be formed around the dendrite structure.

BRIEF DESCRIPTION OF THE DRAWINGS

The above and/or other aspects will become apparent and more readily appreciated from the following description of exemplary embodiments, taken in conjunction with the accompanying drawings, in which:

FIG. 3A is SEM images.

DETAILED DESCRIPTION

The following description, with reference to the accompanying drawings, is provided to assist in a comprehensive understanding of various exemplary embodiments. It includes various specific details to assist in that understanding but these are to be understood as being merely exemplary. Accordingly, those of ordinary skill in the art will recognize that various changes and modifications of the exemplary embodiments described herein can be made without departing from the scope and spirit of the present disclosure. In addition, descriptions of well-known functions and constructions may be omitted for the purposes of clarity and conciseness.

The terms and words used in the following description and claims are not limited to their bibliographical meanings, but are merely being used by the inventor to enable a clear and consistent understanding of the present disclosure. Accordingly, it should be apparent to those skilled in the art that the following description of various exemplary embodiments is provided for the purposes of illustration only, and not for the purpose of limiting the present disclosure.

It is to be understood that the singular forms "a", "an", and "the" include plural referents unless the context clearly dictates otherwise. Thus, for example, reference to "an object" includes reference to one or more of such objects.

Hereinafter, exemplary embodiments will be described in more detail with reference to Test Examples and Examples, but the present disclosure is not limited thereto. Other applications and modifications of the present disclosure may be readily apparent to a person skilled in the art.

Figure 1:
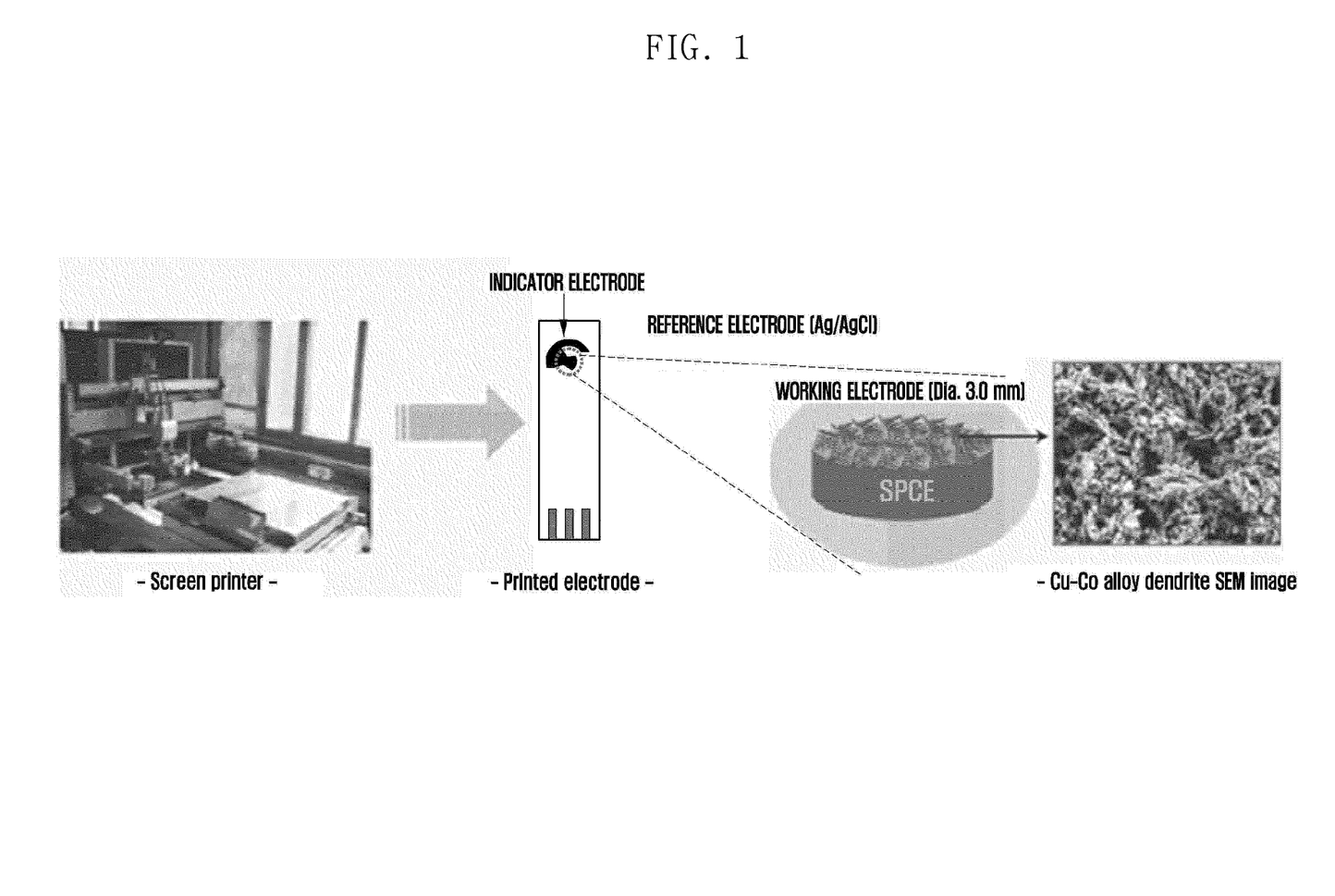
FIG. 1 is a diagram illustrating a type of Cu—Co alloy dendrite electrode that is the working electrode of a non-enzymatic glucose sensor used in an exemplary embodiment.
Figure 2A:
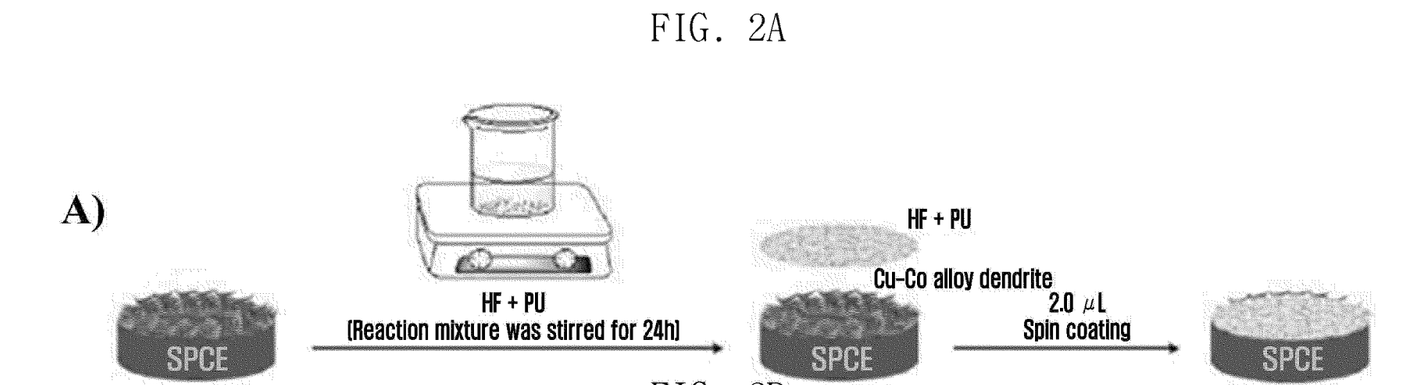
FIGS. 2A and 2B are mimetic diagrams illustrating a process for forming a polymeric film on the working electrode in accordance with an exemplary embodiment.
Figure 2B:
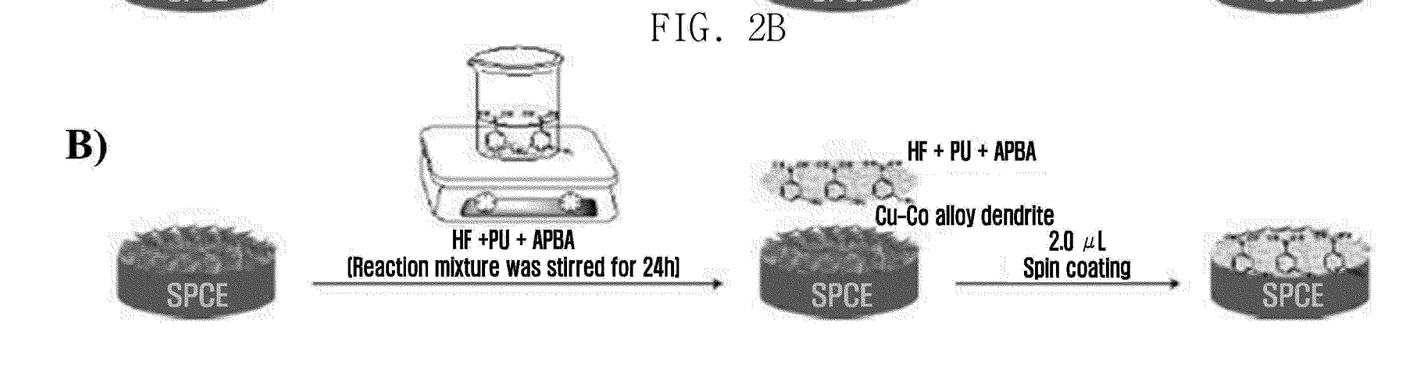

FIG. 1 is a diagram illustrating a type of Cu—Co alloy dendrite electrode that is the working electrode of a non-enzymatic glucose sensor used in an exemplary embodiment. FIGS. 2A and 2B are diagrams illustrating a process for forming a polymeric film on the working electrode in accordance with an exemplary embodiment.

Reference Example 1

Preparation of Cu—Co Alloy Dendrite Electrode

Figure 3A:
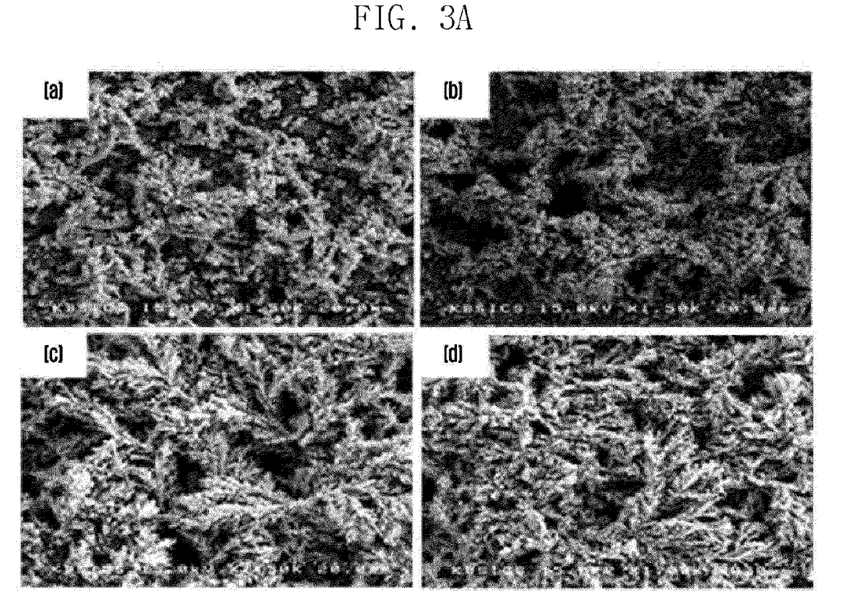

A Cu—Co alloy dendrite electrode, forming a working electrode of a glucose sensor according to an exemplary embodiment was prepared as follows. A Cu—Co alloy dendrite electrode was prepared by performing electrical deposition on the surface of a screen printed carbon electrode (SPCE) by applying a potential of −0.8 V for 50.0 seconds, 75.0 seconds, 100.0 seconds, and 200.0 seconds, respectively, using a chronoamperometry and using 30.0 mM of $CuCl_2$ and $CoCl_2.6H_2O$ in 0.1 M $Na_2SO_4$, electrolyte. Scanning electron microscope (SEM) images of the Cu—Co alloy dendrite surfaces according to the respective electrical deposition times of (a) 50.0 seconds, (b) 75.0 seconds, (c) 100.0 seconds, and (d) 200.0 seconds are illustrated in FIG. 3A. From the results of FIG. 3A, it can be confirmed that in the case of 100.0 seconds of electrical deposition time, the dendrite is more uniformly formed on the SPCE. Therefore, in the following experiments, the Cu—Co alloy dendrite electrode prepared by performing electrical deposition via the application of electricity with a potential of −0.8V for 100.0 seconds.

Figure 3B:
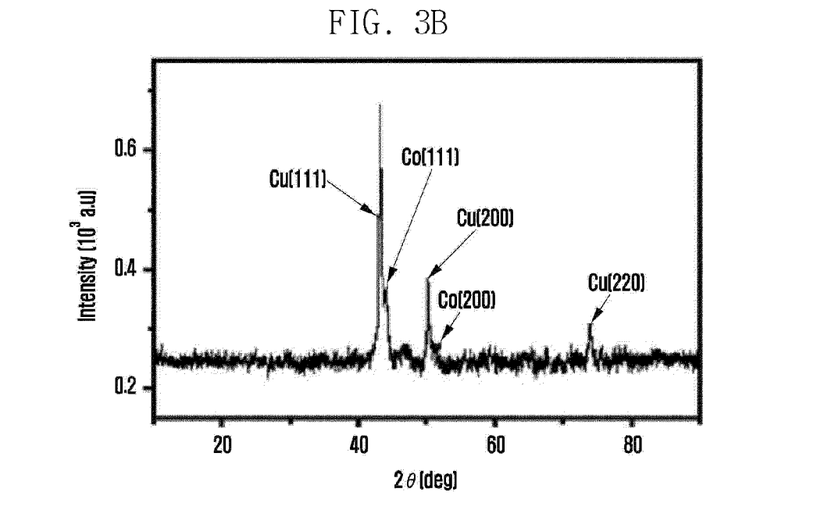
FIG. 3B is a graph showing XRD results illustrating a dendrite structure according the electrical deposition of the Cu—Co alloy dendrite according to Reference Example 1.

In addition, energy dispersive X-ray spectroscopy (EDXS) was used to analyze the Cu—Co alloy dendrite electrode prepared as described above and the composition ratios (in atomic %) of Cu and Co were found to be: for the whole dendrite, Cu was 48.8% and Co was 51.2%; for the stem part, Cu was 49.3% and Co was 50.7%; and for the branch part, Cu was 54.9% and Co was 45.1%. From such results, it can be confirmed that the electrically deposited dendrite is formed in a ratio of Cu:Co=1:1. In addition, from time-of-flight secondary ion mass spectrometry (TOF-SIMS) analysis results, it can be confirmed that the dendrite has a hierarchical structure, independently. FIG. 3B illustrates the X-ray diffractometry (XRD) measuring result that accurately confirms the micro crystal structure of the Cu—Co alloy dendrite synthesized via an electrochemical method. It can be confirmed that, in terms of 2θ values, the respective main peaks corresponding to 43°, 50°, and 73° as the Cu peaks and 44° and 51° as the Co peaks are exhibited.

Reference Example 2

Confirmation of Glucose Oxidation of a Cu—Co Alloy Dendrite Electrode

In order to analyze the glucose oxidation reaction mechanism of a Cu—Co alloy dendrite electrode, controlled potential coulometry (CPC) and high-performance liquid chromatography-electrospray ionization mass (HPLC-ESI MS) were used. According to the electron number involved in the oxidation reaction in the case of glucose, the reaction products of gluconolactone (2-electron oxidation product (EOP)), 2-keto-gluconate (4-EOP), glycelate (4-EOP), glycolate (6-EOP), glucalate (6-EOP), glyoxatlylate (12-EOP), formate (12-EOP), oxalate (18-EOP), $CO_2$, and $H_2O$ (24-EOP) were determined and the reaction products to be expected using a solution subjected to electrolysis using HPLC-ESI MS and a standard solution were determined. From the CPC results obtained in a solution having 1.0 µM of glucose included in 5.0 mL blank (0.1 M of NaOH), it could be confirmed that the quantity of electricity (Q) was constantly maintained for 6,000 seconds or less, and at this time, the quantity of electricity was 5.8 mC. From this result, it can be confirmed that the oxidation reaction product is formate having an electron number of 12.02±0.15. In addition, from the HPLC-ESI MS analysis result, it can be confirmed that since 90.4% or more of the product is confirmed as being formate, the Cu—Co alloy dendrite electrode exhibits a glucose oxidation reaction.

Reference Example 3

Confirmation of the Sensitivity of a Cu—Co Alloy Dendrite Electrode to Saccharides In order to confirm the saccharides selectivity of a non-enzymatic glucose electrode without the polymeric film according to the present disclosure, oxidation reactions to various saccharides were tested using the Cu—Co alloy dendrite electrode (100.0 seconds of electrical deposition time) prepared in Reference Example 1. For such an electrode, a scanning speed of 100.0 mV/s in the potential range of −0.1 V to +0.85 V was applied by using linear sweep voltammetry in a solution of 0.1 M NaOH including each of a blank (0.1 M of NaOH), and 5.0 mM of the respective monosaccharide (glucose, galactose, mannose, fructose, and xylose) and the respective disaccharide (sucrose, lactose, and maltose). The results thus obtained are illustrated in FIG. 4.

Figure 4:
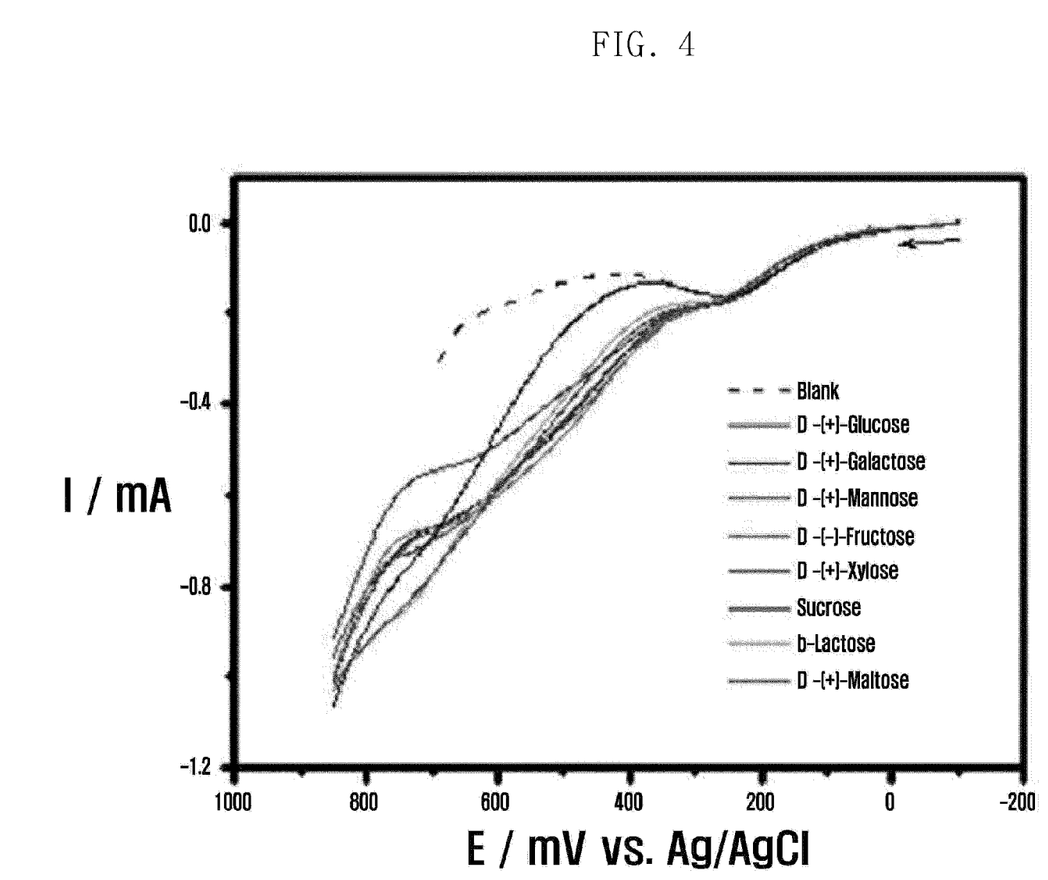
FIG. 4 is a graph illustrating a linear sweep voltammetry (LSV) result of monosaccharides (glucose, galactose, mannose, fructose, xylose) and disaccharides (sucrose, lactose, maltose) using the working electrode without the polymeric film according to an exemplary embodiment in Reference Example 3.

As can be seen in FIG. 4, the monosaccharides oxidation current intensity was 0.526 mA in the case of glucose, 0.497 mA in the case of galactose, 0.514 mA in the case of mannose, 0.510 mA in the case of fructose, and 0.363 mA in the case of xylose; and the disaccharides oxidation current intensity was 0.506 mA in the case of sucrose, 0.668 mA in the case of lactose, and 0.643 mA in the case of maltose. Among the monosaccharides, mannose and fructose exhibited 97.8% and 97.0% of the current intensities as compared to glucose, and among the disaccharides, lactose exhibited 130.8% of the highest current intensity as compared to glucose. From such results, it can be confirmed that the Cu—Co alloy dendrite electrode exhibits sensitivity to all of the saccharides, and the sensitivity to disaccharides is higher than that to monosaccharides.

Reference Example 4

Confirmation of Saccharides Selectivity of Polymeric Film

In order to confirm the selective functionality of each of the polymeric films, after forming each of the polymeric films (Nafion® (NF), poly(vinylidene fluoride) (PVDF), cellulose acetate (CA), chitosan (CT), poly(ethyleneimine) (PEI), poly(ethylene glycol) (PEG), and polyurethane (PU)) on a Cu—Co alloy dendrite/SPCE, the sensitivity to saccharides was estimated using an electrode having activated glucose. In detail, the polymeric films were formed by dropping 10.0 µL of a solution having 1.0 wt % of each of NF, PVDF, CA, CT, PEI, PEG, and PU one time on the Cu—Co alloy dendrite/SPCE prepared in Reference Example 1; spin-coating (JD Tech, model JSPA series—Analog type, S. Korea) at 3,000 rpm; and drying in a vacuum drier at a temperature of 50° C. and a humidity of 90% for 5 minutes. The electrode included in the polymeric film thus formed was subjected to one cycle for the activation into glucose with a scanning speed of 100.0 mV/s in a potential range of −0.1 to +0.85 V in a solution of 0.1 M NaOH including a solution of 10.0 mM glucose using a cyclic voltammetry method. Then, in the 0.1 M NaOH solution that included 10.0 mM of each of monosaccharides (glucose and mannose) and disaccharides (lactose), the sensitivity to each of the saccharides was measured at a scanning speed of 100.0 mV/s in a potential range of −0.1 V to +0.85 V using linear sweep voltammetry. The results thus obtained are listed in Table 1.

TABLE 1

| Polymeric film | Saccharides, Δlpa (mA) | | |
|---|---|---|---|
| | Monosaccharides | | Disaccharides |
| | D-(+)-glucose | D-(+)-Mannose | β-lactose |
| 1.0% NF | 0.314 (100%) | 0.190 (60.5%) | 0.158 (50.3%) |
| 1.0% PVDF | 0.388 (100%) | 0.233 (60.1%) | 0.224 (57.7%) |
| 1.0% CA | 0.510 (100%) | 0.508 (99.6%) | 0.500 (98.0%) |
| 1.0% CT | 0.662 (100%) | 0.744 (112.4%) | 0.844 (127.5%) |
| 1.0% PEI | 0.651 (100%) | 0.655 (100.6%) | 0.852 (130.9%) |
| 1.0% PEG | 0.709 (100%) | 0.584 (82.4%) | 0.873 (123.1%) |
| 1.0% PU | 0.621 (100%) | 0.246 (39.5%) | 0.167 (26.9%) |

In the results listed in Table 1, when the polymeric film was formed with a PEG solution, the polymeric film exhibited the highest current intensities, 0.709 mA and 0.873 mA, to glucose and lactose, respectively. In addition, when the polymeric film was formed with a CT solution, the polymeric film exhibited the highest current intensity, 0.744 mA, to mannose, but exhibited sensitivity to all of the saccharides. However, when the polymeric film was formed with a NF solution, the polymeric film exhibited low sensitivity as compared to glucose, for example, 0.190 mA (60.5%) in the case of mannose and 0.158 mA (50.3%) in the case of lactose. When the polymeric film was formed with a PVDF solution, the polymeric film exhibited low sensitivity, for example, 0.233 mA (60.1%) in the case of mannose and 0.244 mA (57.7%) in the case of lactose. In this experiment, as compared to a the polymeric film formed with a PU solution, the selectivity to glucose was mostly excellent, for example, 0.246 mA (39.5%) in the case of mannose and 0.167 mA (26.9%) in the case of lactose.

Test Example 1

Confirmation of Sensitivity According to Saccharide Activation

Sensors formed using a mixed polymeric film of PU and NF, which exhibited most excellent glucose selectivity in the result in Reference Example 3, were activated to each of the saccharides, and then the glucose selectivity was confirmed. As can be seen in FIG. 2A, the polymeric film was formed by dropping 10.0 µL of NF solution prepared by stirring a solution of the weight ratio of PU:NF=1:1 and 3.0% of mixed wt % of PU and NF for 24 hours on a Cu—Co alloy dendrite/SPCE once; spin-coating (JD Tech, model JSPA series—analog type, S. Korea) at 3,000 rpm; and drying in a vacuum drier at a temperature of 50° C. and a humidity of 90% for 5 minutes. The mixed solution was prepared such that the final content of PU+NF was 3.0 wt % by quantity of NF in an ethanol solvent and PU in 0.5 M sulfuric acid.

The polymer/Cu—Co alloy dendrite/SPCEs were activated by performing one cycle in the solutions of 1.0 M NaOH including each of 10.0 mM glucose, mannose, fructose, and lactose independently, using cyclic voltammetry in a potential range of −0.1 to +0.85 V at a scanning speed of 100.0 mV/s. Then, for the polymer/Cu—Co alloy dendrite/SPCEs that were activated with each of the different saccharides, the sensitivities to each of the saccharides were measured using a scanning speed of 100.0 mV/s in a potential range of −0.1 to +0.85 V using linear sweep voltammetry in the solution of 0.1 M NaOH including each of 10.0 mM glucose, mannose, fructose, and lactose.

When using the electrode that was first activated with lactose, there was a low current density to glucose, 0.064 mA (12.1%), 0.066 mA (12.5%), and 0.051 mA (9.7%) in the cases of mannose, glucose, and fructose, respectively, as compared with lactose; and when using the electrode that was first activated with mannose, 0.054 mA (16.4%), 0.034 mA (10.3%), and 0.048 mA (14.6%) in the cases of glucose, lactose, and fructose, respectively, as compared with mannose. However, when using the electrode that was first activated with glucose, it was confirmed that it exhibited sensitive current values at a low level, that is, 0.062 mA (18.1%), 0.059 mA (17.3%), and 0.053 mA (15.5%) in the case of mannose, fructose, and lactose, respectively, as compared with glucose.

Test Example 2

Comparison of Glucose Selectivities According to the Content of NF and PU

In order to compare the changes in glucose selectivities according to the content of NF and PU in the polymeric film, polymer/Cu—Co alloy dendrite/SPCEs were formed in the same manner as in Test Example 1, using the respective solutions of 0.5, 1.0, 3.0, and 5.0 wt % of mixed NF and PU, and then were activated with glucose. Then, the sensitivities to each of the saccharides of the polymer/Cu—Co alloy dendrite/SPCEs were measured by applying a scanning speed of 100.0 mV/s in a potential range of −0.1 to +0.85 V using linear sweep voltammetry in solutions of 0.1 M NaOH including each of 10.0 mM glucose, mannose, fructose, and lactose. The results thus obtained are listed in Table 2.

As the solutions of PU and NF, mixed solutions were prepared such that the mixed final contents of PU and NF were 0.5, 1.0, 3.0, and 5.0 wt %, respectively, by quantity of NF in an ethanol solvent and PU in 0.5 M sulfuric acid.

TABLE 2

| | Saccharides, Δlpa (mA) | | | |
|---|---|---|---|---|
| | Monosaccharides | | | |
| Electrode configuration | D-(+)-glucose | D-(+)-mannose | D-(−)-fructose | Disaccharides β-lactose |
| 0.5% NF + PU/Cu—Co/SPCE | 0.357 (100%) | 0.295 (82.6%) | 0.267 (74.7%) | 0.238 (66.7%) |
| 1.0% NF + PU/Cu—Co/SPCE | 0.356 (100%) | 0.176 (49.4%) | 0.168 (47.2%) | 0.101 (28.3%) |
| 3.0% NF + PU/Cu—Co/SPCE | 0.345 (100%) | 0.063 (18.2%) | 0.061 (17.7%) | 0.054 (15.7%) |
| 5.0% NF + PU/Cu—Co/SPCE | 0.290 (100%) | 0.062 (21.3%) | 0.059 (20.3%) | 0.047 (16.2%) |

In the results listed in Table 2, the current intensities of the respective electrodes to each of 10.0 mM glucose, mannose, fructose, and lactose were 0.357 mA, 0.295 mA, 0.267 mA, and 0.238 mA, respectively, when using 0.5% polymeric film. In addition, they were 0.356 mA, 0.176 mA, 0.168 mA, and 0.101 mA, respectively, when using 1.0% polymeric film; 0.345 mA, 0.063 mA, 0.061 mA, and 0.054 mA, respectively, when using 3.0% polymeric film; and 0.290 mA, 0.062 mA, 0.059 and 0.047 mA when using 5.0% polymeric film. With respect to the polymeric film mixed with NF and PU, as the concentrations thereof increased, the current intensity of glucose oxidation decreased. In addition, with respect to the 0.5% polymeric film having the lowest concentration of polymeric film, the highest glucose oxidation current value was exhibited, but low selectivity to glucose was exhibited, that is, the levels of 82.6%, 74.7%, and 66.7% in the case of mannose, fructose, and lactose, respectively, as compared with glucose. On the other hand, it can be seen that when using 3.0% polymeric film mixed with NF and PU, that example exhibited the highest glucose selectivities, that is, the levels of 18.2%, 17.7%, and 15.7% in the case of mannose, fructose, and lactose, respectively, as compared with glucose.

Test Example 3

Comparison of Selectivities According to the Preparation Temperature

As can be seen in FIG. 2A, polymeric films were formed by dropping 10.0 μL of a NF solution prepared by stirring a solution having a weight ratio of PU:NF=1:1 and 3.0% of mixed PU and NF for 24 hours on a Cu—Co alloy dendrite/SPCEs once; spin-coating (JD Tech, model JSPA series—analog type, S. Korea) at 3,000 rpm; and drying in a vacuum drier at the respective temperatures of 25° C., 50° C., and 75° C., and a humidity of 90% for 5 minutes. The electrode including the polymeric film thus formed was activated with glucose by performing one cycle at a scanning speed of 100.0 mV/s in a potential range of −0.1 V to +0.85 V using cyclic voltammetry in a solution of 0.1 M NaOH including 10.0 mM of glucose. Then, the sensitivities of the activated polymer/Cu—Co alloy dendrite/SPCEs to the respective saccharides were measured by applying a scanning speed of 100.0 mV/s in a potential range of −0.1 V to +0.85 V using linear sweep voltammetry in a solution of 0.1 M NaOH including each of 10.0 mM glucose, mannose, fructose, and lactose.

The oxidation current densities of 10.0 mM glucose, mannose, fructose, and lactose, respectively, were 0.433 mA, 0.208 mA, 0.0185 mA, and 0.034 mA, respectively, for the 25° C. sample; 0.345 mA, 0.063 mA, 0.061 mA, and 0.054 mA, respectively, for the 50° C. sample; and 0.407 mA, 0.171 mA, 0.164 mA, and 0.158 mA, respectively, for the 75° C. sample. With respect to the 25° C. sample, mannose and fructose exhibited the lowest selectivities, that is, the levels of 48.3% and 42.7%, respectively, as compared with glucose, but lactose exhibited the highest selectivity, that is, 7.8% as compared with glucose. With respect to glucose selectivity to saccharides, it was confirmed that when the preparation temperature is 50° C., mannose, fructose, and lactose exhibited the highest selectivities, that is, the levels of 18.2%, 17.7%, and 15.7%, respectively, as compared with glucose.

Test Example 4

Effect of APBA Addition

As can be seen in FIG. 2B, polymeric films further including APBA were formed by dropping 2.0 μL of an APBA solution and 10.0 μL of NF+PU mixed solution prepared by stirring a solution having a weight ratio of PU:NF=1:1 and 3.0% of mixed PU and NF and each of 0.5 mM, 1.0 mM, and 3.0 mM of amino phenyl boronic acid (APBA) for 24 hours on the Cu—Co alloy dendrite/SPCEs once; spin-coating (JD Tech, model JSPA series—analog type, S. Korea) at 3,000 rpm; and drying in a vacuum drier at a temperature of 50° C. and a humidity of 90% for 5 minutes. After forming the polymeric films, the electrode including the polymeric film thus formed was activated with glucose by performing one cycle at a scanning speed of 100.0 mV/s in a potential range of −0.1 V to +0.85 V using cyclic voltammetry method in a solution of 0.1 M NaOH including 10.0 mM of glucose. Then, the sensitivities of the activated polymer/Cu—Co alloy dendrite/SPCEs to the respective saccharides were measured by applying a scanning speed of 100.0 mV/s in a potential range of −0.1 V to +0.85 V using linear sweep voltammetry in a solution of 0.1 M NaOH including each of 10.0 mM glucose, mannose, fructose, and lactose. The results thus obtained are illustrated in FIGS. 5A, 5B and 5C and listed in Table 3.

TABLE 3

| | Saccharides, Δlpa (mA) | | | |
|---|---|---|---|---|
| | Monosaccharides | | | |
| Electrode configuration | D-(+)-glucose | D-(+)-mannose | D-(−)-fructose | Disaccharides β-lactose |
| 3.0% NF + PU + 0.5 mM APBA/Cu—Co/SPCE | 0.563 (100%) | 0.221 (39.4%) | 0.203 (36.1%) | 0.084 (14.9%) |
| 3.0% NF + PU + 1.0 mM APBA/Cu—Co/SPCE | 0.654 (100%) | 0.121 (18.5%) | 0.115 (17.6%) | 0.021 (3.2%) |
| 3.0% NF + PU + 3.0 mM APBA/Cu—Co/SPCE | 0.659 (100%) | 0.151 (22.9%) | 0.146 (22.2%) | 0.052 (7.9%) |

Figure 5A:
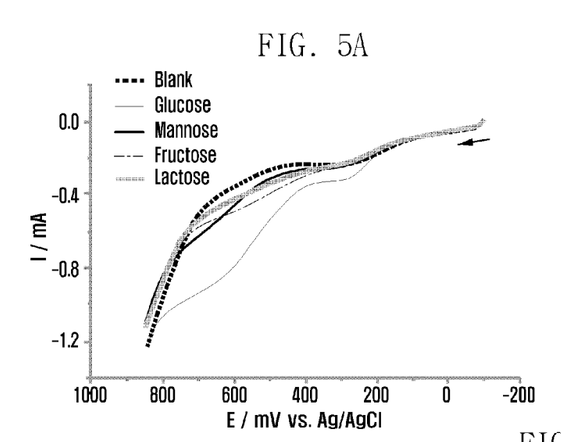
FIGS. 5A, 5B and 5C are graphs illustrating LSV results of monosaccharides (glucose, mannose, fructose) and disaccharides (lactose) using different concentrations of APBA in the composition of the polymeric film according to an exemplary embodiment in Test Example 5 ((5A) 0.5 mM of APBA, (5B) 1.0 mM of APBA, and (5C) 3.0 mM of APBA).
Figure 5B:
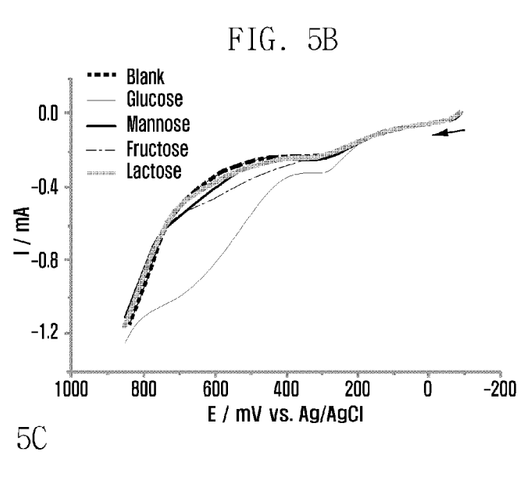
Figure 5C:
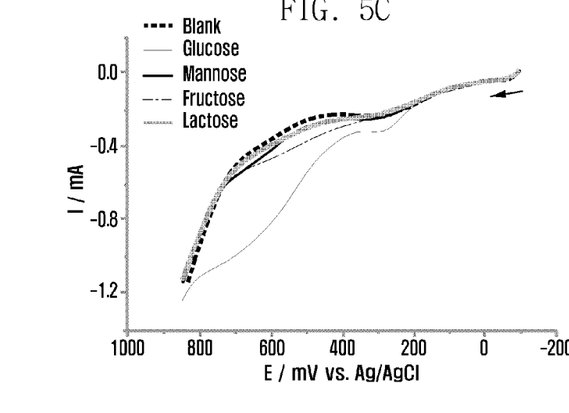

As can be seen in FIGS. 5A, 5B and Table 3, the oxidation current intensities of the respectively modified electrodes according to concentrations of APBA to 10.0 mM glucose, mannose, fructose, and lactose were 0.563 mA, 0.221 mA, 0.203 mA, and 0.084 mA, respectively, when using 0.5 mM of APBA; 0.0654 mA, 0.121 mA, 0.115 mA, and 0.021 mA, respectively, when using 1.0 mM of APBA; and 0.659 mA, 0.151 mA, 0.146 mA, and 0.052 mA, respectively, when using 3.0 mM of APBA. As the concentration of APBA was increased, the current intensity of glucose oxidation also increased. When using 1.0 mM of APBA, mannose, fructose, and lactose exhibited sensitivities in the levels of 18.5%, 17.6%, and 3.2%, respectively, as compared with glucose. In addition, when using APBA as compared to not using APBA, the oxidation current intensities of the respective saccharides exhibited two or more times improved sensitivities. Therefore, in this case, it was confirmed that sensitivities at the levels of 98.1% and 99.9% to ~10 mg/dL mannose and lactose present in blood, respectively, were exhibited, and sensitivities at the levels of 94.6% to the fructose in a concentration of 30 mg/dL or less were exhibited.

However, with respect to the sample including 3.0 mM of APBA, the Cu—Co alloy dendrite electrode was coated with excess APBA, and thereby, the oxidation catalyst reaction of the dendrite electrode to glucose was inhibited. Therefore, it was considered that the sensitivity to glucose was slightly reduced.

Test Example 5

Effect of the Organic Material on Reducing Blocking Action

To be added to the Cu—Co alloy dendrite/SPCE without the polymeric film prepared in Reference Example 1, 3% NF+PU/Cu—Co alloy dendrite/SPCE prepared as described in Test Example 1, and 3.0% NF+PU+1.0 mM APBA/Cu—Co alloy dendrite/SPCE prepared in Test Example 4 were prepared. The electrodes were activated with glucose by performing one cycle at a scanning speed of 100.0 mV/s in a potential range of −0.1 V to +0.85 V using cyclic voltammetry in a solution of 0.1 M NaOH including a solution of 10.0 mM glucose. Then, the current intensities to the respective components were measured by subjecting the activated electrodes thus obtained at a scanning speed of 100.0 mV/s in a potential range of −0.1 V to +0.85 V using linear sweep voltammetry in solutions of 0.1 M NaOH including 10.0 mM glucose, 5.0 mM ascorbic acid (AA), and 5.0 mM acetaminophen (AP), respectively. The results thus obtained are listed in Table 4.

TABLE 4

| Electrode configuration | D-(+)-glucose | Ascorbic acid (AA) | Acetaminophen (AP) |
| --- | --- | --- | --- |
| Cu—Co/SPCE | 1.096 mA (100%) | 0.195 mA (17.8%) | 0.026 mA (2.3%) |
| 3.0% NF + PU/Cu—Co/SPCE | 0.345 mA (100%) | — (0.0%) | — (0.0%) |
| 3.0% NF + PU + 1.0 mM APBA/Cu—Co/SPCE | 0.654 mA (100%) | — (0.0%) | — (0.0%) |

As seen in Table 4, in the sample of Cu—Co/SPCE not including a polymeric film, the current intensities to 10.0 mM glucose, 5.0 mM AA, and 5.0 mM AP, respectively, were 1.096 mA, 0.195 mA (17.8%), and 0.026 mA (2.3%), respectively. However, it was confirmed that when using 3.0% NF+PU/Cu—Co/SPCE and 3.0% NF+PU+1.0 mM APBA/Cu—Co/SPCE using the polymeric film and APBA, blocking action against AA and AP can be entirely removed.

Test Example 6

Analysis of the Sensitive Range of the Sensor to Glucose

As described in Test Example 4, 3.0% NF+PU+1.0 mM APBA/Cu—Co/SPCE was formed and then activated with glucose. Then, changes in current intensities were confirmed by applying a glucose oxidation potential of +0.65 V to the activated 3.0% NF+PU+1.0 mM APBA/Cu—Co/SPCE thus obtained in solutions of 0.1 M NaOH including different glucose concentrations in a range of 1.0 µM to 25.0 mM. The results thus obtained are illustrated in FIG. 6.

Figure 6A:
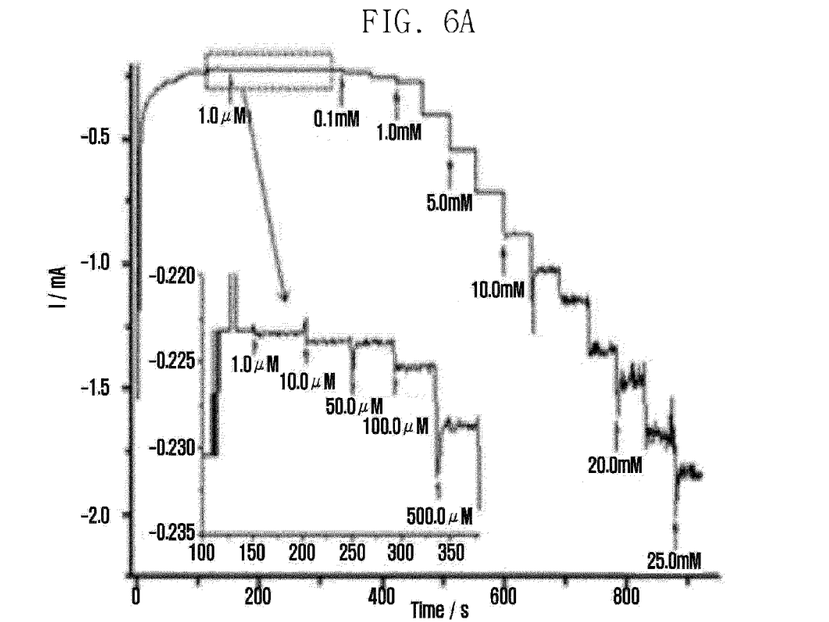
FIGS. 6A and 6B are graphs illustrating a chronoamperogram and a calibration plot as a function of glucose concentration change (1.0 μM to 25.0 mM) of a non-enzymatic glucose sensor comprising the polymeric film according to an exemplary embodiment in Test Example 6, in which the inset graphs are expanded views of the 1.0 μM to 500.0 μM glucose concentration range.
Figure 6B:
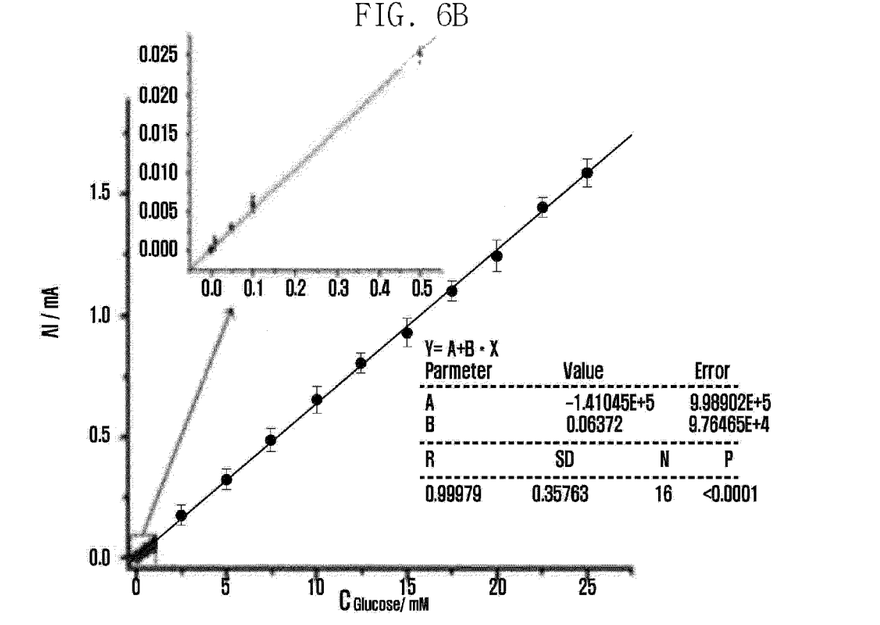

FIG. 6A is a chronoamperogram illustrating changes in current intensities at various glucose concentrations in a range of 1.0 µM to 25.0 mM by applying a glucose oxidation potential of +0.65 V. From FIG. 6B, it can be seen that as the concentration of glucose increases, the oxidation current intensity also increases. FIG. 6B is a calibration plot regarding the results obtained from the chronoamperogram. The linear regression equation is Alp (mA)=(0.00101±0.00009)+(0.06377±0.0009) [C] (mM) and the correlation coefficient is 0.999. From this result, it can be seen that the dynamic range of the glucose sensor is present over the range of 1.0 µM to 25.0 mM, and the detection limit is 0.5±0.02 µM (RSD <5%). From this result, it can be seen that the Cu—Co alloy dendrite material has excellent sensitivity to glucose in a wide range of concentrations, from low concentration to high concentration.

Test Example 7

Analysis of Simulated Blood

Figure 7A:
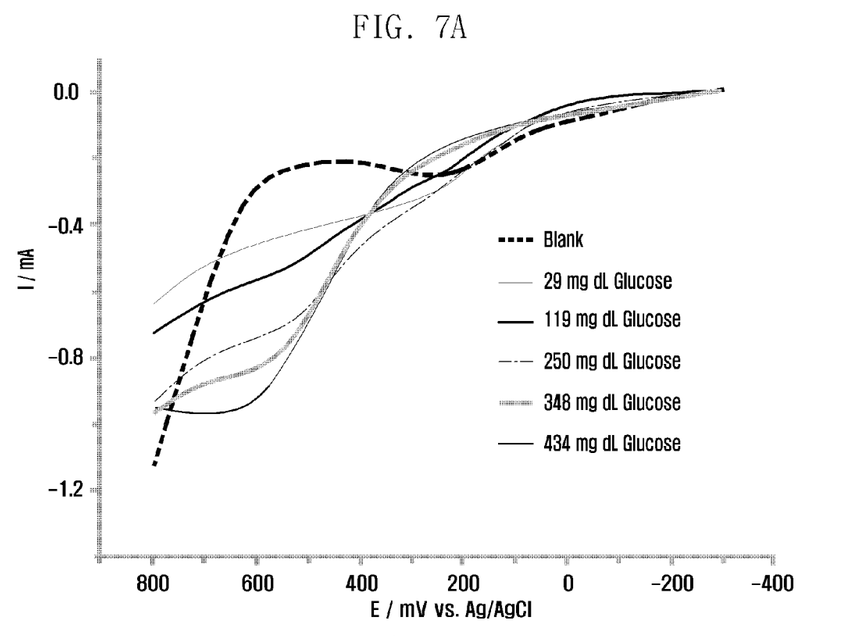
FIGS. 7A and 7B are graphs illustrating the results and a calibration plot of the results of measuring LSV against the simulated blood glucose concentrations in five sections of 29, 119, 250, 348, and 434 mg/dL in Test Example 7.
Figure 7B:
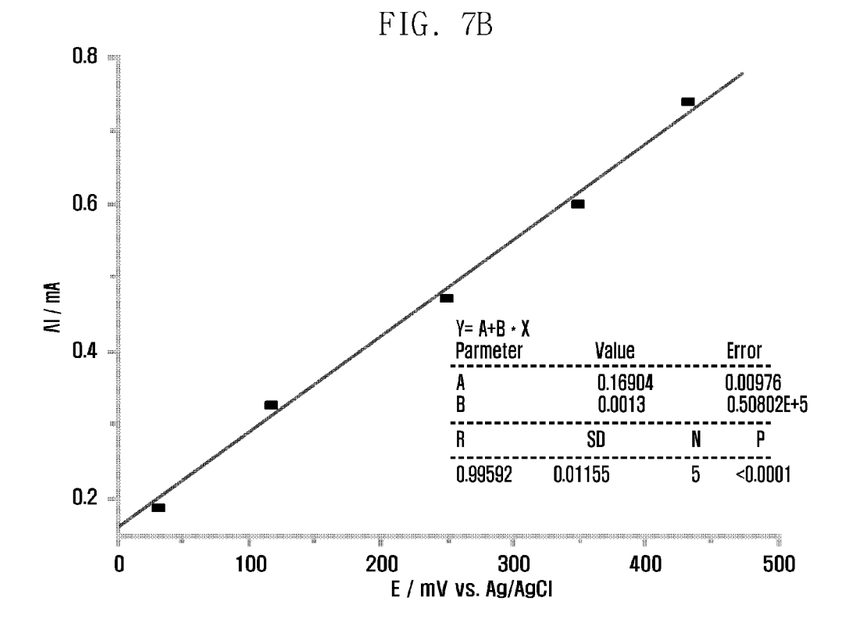

By using the same method as Test Example 6, a 3.0% NF+PU+1.0 mM APBA/Cu—Co/SPCE was formed, and then a glucose detection experiment in simulated blood was performed by using the glucose sensor that was activated with glucose. The glucose detection strength was measured in simulated blood having hematocrit concentrations of 27, 42, and 47%, and it could be seen that as the hematocrit concentration was increased, the glucose detection strength was decreased. For this reason, each of the simulated blood samples were diluted with saline solution to be 10% hematocrit concentration, and then by adding a standard glucose thereto, simulated blood having five different glucose concentrations (29 mg/dL, 119 mg/dL, 250 mg/dL, 348 mg/dL, and 434 mg/dL) was prepared. By using the prepared simulated blood, LSV to a blank (black dash line) and simulated blood having 5 glucose concentrations (29 mg/dL, 119 mg/dL, 250 mg/dL, 348 mg/dL, 434 mg/dL, and red solid line) were measured. The results thus obtained are illustrated in FIGS. 7A and 7B. From the results illustrated in FIGS. 7A and 7B, it can be seen that linearity was exhibited in the glucose concentrations of from 29 to 434 mg/dL (FIG. 5B).

According to the polymeric film composition of the exemplary embodiments, selectivity of saccharides by a non-enzymatic glucose sensor, inhibition of blocking action by an organic material, and improvement of sensitivity can be achieved. Therefore, by using the glucose sensor, it is possible to measure hypoglycemia and hyperglycemia in a concentration range that covers practical measurement. In addition, even when body fluid having a relatively low concentration of glucose, other than blood, is used as an object, it is capable of achieving the measurement of blood sugar with high sensitivity.

While exemplary embodiments have been particularly exhibited and described with reference to an examples, it will be understood by those skilled in the art that various changes in form and details may be made therein without departing from the spirit and scope of the inventive concept.

What is claimed is:

1. A non-enzymatic glucose sensor comprising:
a reference electrode;
a working electrode electrically connected to the reference electrode; and
a polymeric film provided on a surface of the working electrode,
wherein the polymeric film comprises polyurethane, perfluorosulfonic acid polymer and amino phenyl boronic acid,
wherein an amount of the polyurethane and perfluorosulfonic acid polymer is 3.0 wt % with respect to a total weight of the polymeric film, and
an amount of the amino phenyl boronic acid is 0.05 wt % to 0.3 wt % with respect to a total weight of the polymeric film.

2. The non-enzymatic glucose sensor of claim 1, wherein the surface of the working electrode comprises a single metal or an alloy of a plurality of metals.

3. The non-enzymatic glucose sensor of claim 2, wherein the single metal or the alloy of a plurality of metals on the surface of the working electrode comprises any one single metal or an alloy of two or more of the single metals selected from a group consisting of Cu, Au, Zn, Mn, Ni, and Co.

4. The non-enzymatic glucose sensor of claim 3, wherein the surface of the working electrode comprises a Cu—Co alloy.

5. The non-enzymatic glucose sensor of claim 4, wherein within the Cu—Co alloy, an atomic percentage of Cu is from 45-65% and an atomic percentage of Co is from 35-55%.

6. The non-enzymatic glucose sensor of claim 1, wherein the working electrode is a microporous metal electrode.

7. The non-enzymatic glucose sensor of claim 6, wherein a diameter of micropores in the microporous metal electrode is 100 nm to 5 μm, and a porosity of the microporous metal electrode is 5% to 15%.

8. The non-enzymatic glucose sensor of claim 1, wherein the working electrode is a dendrite electrode.

9. The non-enzymatic glucose sensor of claim 1, wherein the working electrode is formed by electrical deposition on a carbon electrode or a copper plate.

10. The non-enzymatic glucose sensor of claim 9, wherein the working electrode is formed on a glassy carbon electrode or a copper plate by electrical deposition for 75 to 200 seconds with a potential of −0.6 V to −1.2 V.

11. The non-enzymatic glucose sensor of claim 1, wherein the polymeric film is formed by drying the polymeric film at a temperature of 25° C. to 75° C.

12. The non-enzymatic glucose sensor of claim 5, wherein the atomic percentages of Cu and Co equal 100 atomic percent of the surface of the working electrode.

* * * * *